US009964401B2

(12) United States Patent
Deschenes et al.

(10) Patent No.: US 9,964,401 B2
(45) Date of Patent: May 8, 2018

(54) INSPECTION SYSTEM FOR INSPECTING AN OBJECT AND INSPECTION METHOD FOR SAME

(71) Applicant: POLYRIX INC., Québec (CA)

(72) Inventors: Jean-Daniel Deschenes, Québec (CA); Philippe Lambert, Québec (CA); Nicolas Martel-Brisson, Québec (CA); Sébastien Quirion, Québec (CA)

(73) Assignee: POLYRIX INC., Quebec, Quebec (CA)

( * ) Notice: Subject to any disclaimer, the term of this patent is extended or adjusted under 35 U.S.C. 154(b) by 114 days.

(21) Appl. No.: 14/905,740

(22) PCT Filed: Jul. 9, 2014

(86) PCT No.: PCT/CA2014/050651
§ 371 (c)(1),
(2) Date: Jan. 15, 2016

(87) PCT Pub. No.: WO2015/006865
PCT Pub. Date: Jan. 22, 2015

(65) Prior Publication Data
US 2016/0169665 A1  Jun. 16, 2016

Related U.S. Application Data

(60) Provisional application No. 61/846,844, filed on Jul. 16, 2013.

(51) Int. Cl.
G01B 11/24 (2006.01)
G01B 11/25 (2006.01)
(Continued)

(52) U.S. Cl.
CPC ............ G01B 11/25 (2013.01); G01B 11/002 (2013.01); G01B 11/245 (2013.01); G01N 21/8806 (2013.01)

(58) Field of Classification Search
CPC ....... G01B 11/25; G01B 11/24; G01B 11/002; G01B 11/30; G01N 21/8806; G01N 21/89;
(Continued)

(56) References Cited

U.S. PATENT DOCUMENTS 4,529,316 A * 7/1985 DiMatteo ............... G01B 11/24
356/3.03
6,690,474 B1 * 2/2004 Shirley ............... G01B 11/2527
356/512
(Continued)

FOREIGN PATENT DOCUMENTS

WO   2006/078684 A2   7/2006
WO   2011/056196 A1   5/2011

OTHER PUBLICATIONS

Extended European Search Report for corresponding European Patent Application No. 14826074.8 dated Dec. 21, 2016, 9 pgs.
(Continued)

Primary Examiner — Hoa Pham
(74) Attorney, Agent, or Firm — Merchant & Gould P.C.

(57) ABSTRACT

A system for inspecting an object has at least one light projector and at least one camera jointly defining a field of view and a computer operatively connected thereto. The computer is configured to acquire object data representative of the outer surface of the object through projection of light thereon by the light projector and acquisition of return light by the camera. The object data relates surface points on the outer surface of the object to one or more source point of the light projector. The computer is further configured to generate inspection information data based on the acquired object data and project the inspection information data on at least some of the surface points of the outer surface of the object using the corresponding source points of the at least
(Continued)

one light projector. A method inspects an outer surface of an object.

14 Claims, 5 Drawing Sheets

(51) Int. Cl.
    *G01B 11/245*     (2006.01)
    *G01N 21/88*     (2006.01)
    *G01B 11/00*     (2006.01)

(58) Field of Classification Search
    CPC ...... G01N 21/94; G01N 29/048; G03B 29/00; G03B 31/00
    USPC .................................................. 356/601–623
    See application file for complete search history.

(56) References Cited

U.S. PATENT DOCUMENTS

| | | | | |
|---|---|---|---|---|
| 8,848,201 | B1* | 9/2014 | Bruce | G01B 11/24 356/601 |
| 8,970,823 | B2* | 3/2015 | Heidemann | G01B 11/25 356/2 |
| 2003/0002052 | A1* | 1/2003 | Hoffmann | G01B 11/2518 356/603 |
| 2004/0189944 | A1 | 9/2004 | Kaufman et al. | |
| 2007/0025612 | A1 | 2/2007 | Iwasaki et al. | |
| 2007/0127015 | A1 | 6/2007 | Palmateer et al. | |
| 2009/0059241 | A1* | 3/2009 | Lapa | G01B 11/2518 356/603 |
| 2011/0019155 | A1 | 1/2011 | Daniel et al. | |
| 2011/0169924 | A1 | 7/2011 | Haisty et al. | |
| 2012/0057174 | A1 | 3/2012 | Briggs | |
| 2012/0099798 | A1* | 4/2012 | Saruta | G01B 11/002 382/203 |
| 2013/0293684 | A1* | 11/2013 | Becker | G01B 11/245 348/47 |
| 2014/0168662 | A1* | 6/2014 | Takabayashi | G01B 11/2513 356/610 |
| 2014/0226167 | A1* | 8/2014 | Smith | G03B 21/14 356/614 |
| 2014/0293009 | A1* | 10/2014 | Nakazato | H04N 13/0253 348/46 |
| 2015/0085108 | A1* | 3/2015 | Kaufman | G01B 11/24 348/135 |
| 2015/0260509 | A1* | 9/2015 | Kofman | G01B 11/2513 356/601 |

OTHER PUBLICATIONS

International Search Report for corresponding International Patent Application No. PCT/CA2014/050651 dated Oct. 9, 2014.

\* cited by examiner

INSPECTION SYSTEM FOR INSPECTING AN OBJECT AND INSPECTION METHOD FOR SAME

This application is a National Stage Application of PCT/CA2014/050651, filed 9 Jul. 2014, which claims benefit of U.S. Provisional Application Ser. No. 61/846,844, filed 16 Jul. 2013 and which applications are incorporated herein by reference. To the extent appropriate, a claim of priority is made to each of the above disclosed applications.

FIELD OF THE INVENTION

The present invention relates to the field of object inspection. More particularly, it relates to a three dimensional inspection system for inspecting an object and to an inspection method for same.

BACKGROUND

Quality control is a constant concern in the manufacturing industry. Therefore, numerous tools have been developed over time to assist operators in performing inspection of manufactured objects at different stages of the manufacturing process.

For example, several systems and corresponding methods of operation are known in the art to perform computerized dimensional and visual inspection of an object. Such systems typically capture object data relative to the object for subsequent processing by the system and visualisation by a user. Typically, inspection data generated by processing of the captured object data is visualized either on a display screen of a computer, using a three dimensional visualisation software where the inspected object, along with the inspection information overlaid on the object, can be rotated and inspected, or on a printout where specific viewpoints showing the inspected object and inspection information are presented.

Known systems however tend to suffer from several drawbacks. In particular, the visualisation of the inspected object and inspection information on a display screen or a printout copy with specific viewpoints can lead to misconceptions between what is displayed on the screen or printout and the corresponding regions of the inspected object. For example, and without being limitative, in a case where a specific region of the inspected object is targeted as needing to be reworked, an erroneous interpretation of the relationship between the displayed information and the physical object which is inspected can lead to faulty identification of the targeted region of the object. In other words, an operator can confuse the targeted region with another region of the inspected object and consequently proceed to rework the wrong region. Such misconceptions are especially likely to occur in cases where the object is symmetrical and can lead to the original defect remaining uncorrected and still be present on the final object. Such misconceptions can be costly, time consuming and potentially dangerous if the region that was not properly reworked is critical.

The applicant is also aware of inspection systems where video-projectors are used to display the inspection information directly on the object. Once again, however, known systems tend to suffer from several drawbacks.

For example, PCT patent application No. WO2011/056196 teaches the use of a video-projector to display assembly related information on an object in a substantially undistorted manner during assembling steps. However, the video-projector of the device disclosed in the application is not configured to capture object data relative to the specific shape of the outer surface of the object being inspected or assembled. Consequently, the system disclosed in this application cannot be used to generate inspection information based on the acquired object data, such as portions of the outer surface of the object that are faulty or non-conforming with a reference, which is often valuable for operators in the inspection process.

PCT patent application No. WO2006/078684 and US patent application No. 2004/0189944 teach the use of a digitizer scanner to acquire a three dimensional profile of the object and a distinct laser projection device to project information onto it. As will be easily understood, the use of distinct devices for acquiring the three dimensional profile of the object and to project onto it requires the use of a calibration mean to calibrate both devices with respect to one another or with respect to the inspected object, in order for the distinct devices to work in combination. Moreover, such a system is not cost efficient as it duplicates the components included in the system. In addition, the laser projection device of known devices cannot project color information, can flicker due to the fact that the laser must sweep all the lines of the projected information, displays speckle and are not eye-safe.

In view of the above, there is a need for an improved three dimensional inspection system and corresponding method of operation, which would be able to overcome or at least minimize some of the above-discussed prior art concerns.

SUMMARY OF THE INVENTION

According to a first general aspect, there is provided a three dimensional inspection system for inspecting an outer surface of an object. The inspection system comprises at least one light projector and at least one camera jointly defining a field of view of the inspection system and a computer operatively connected to the at least one light projector and the at least one camera. The computer is configured to acquire three dimensional object data representative of the outer surface of the object positioned in the field of view through projection of light thereon by the at least one light projector and acquisition of return light by the at least one camera. The three dimensional object data relates surface points on the outer surface of the object to one or more source point of the at least one light projector. The computer is further configured to generate inspection information data based on the acquired three dimensional object data and project the inspection information data on at least some of the surface points of the outer surface of the object using the corresponding source points of the at least one light projector.

In an embodiment, the source points of the at least one light projector each comprise a pixel of one of the at least one light projector.

In an embodiment, the at least one light projector and the at least one camera are configured for the computer to perform acquisition of the three dimensional object data by triangulation.

In an embodiment, the three dimensional object data comprises a point cloud comprising three dimensional spatial coordinates matching corresponding ones of the surface points on the outer surface of the object.

In an embodiment, the inspection information data is based on deviations between the spatial coordinates of the point cloud and a reference object.

In an embodiment, at least one of the at least one light projector and the at least one camera is moveable relative to the object and the computer is further configured to: sense the movement of the at least one of the at least one light projector and the at least one camera; and adapt the projection of the inspection information data according to the sensed movement.

In an embodiment, the at least one camera comprises a numeric camera capturing numeric images of the object.

In an embodiment, the inspection system includes at least two light projectors and the computer is further configured to determine overlap locations of a light projected by the at least two light projectors on the outer surface of the object and fade the light projected by at least one of the at least two light projectors at the overlap locations.

In an embodiment, the three dimensional inspection system comprises a plurality of light projectors and cameras.

In an embodiment, the plurality of light projector and cameras are substantially uniformly distributed around the object.

According to another general aspect, there is also provided a method for inspecting an outer surface of an object. The method comprises the steps of: positioning the object within a field of view of at least one light projector and at least one camera; acquiring three dimensional object data representative of the outer surface of the object positioned in the field of view through projection of light thereon by the at least one light projector and acquisition of return light by the at least one camera, the three dimensional object data relating surface points on the outer surface of the object to one or more source points of the at least one light projector; generating inspection information data based on the acquired three dimensional object data; and projecting the inspection information data on at least some of the surface points of the outer surface of the object using the corresponding source points of the at least one light projector.

In an embodiment, the method further comprises the step of generating a point cloud of three dimensional spatial coordinates matching corresponding ones of the surface points on the outer surface of the object.

In an embodiment, the step of generating the inspection information data comprises the sub-step of determining a deviation between corresponding spatial coordinates of the point cloud and a reference object.

In an embodiment, the step of acquiring the three dimensional object data representative of the outer surface of the object is performed by obtaining the spatial coordinates of points located on the surface of the object by triangulation.

In an embodiment, the method further comprises the steps of: sensing the movement of at least one of the least one light projector and the at least one camera; and adapting the projection of the inspection information data according to the sensed movement.

In an embodiment, at least two light projectors are provided and the method further comprises the steps of: determining overlap locations of a light projected by the at least two light projectors on the outer surface of the object; and fading the light projected by at least one of the at least two light projectors at the overlap locations.

Advantageously, instead of relying on a computer screen to display the acquired information on the object, embodiments of the invention use the same projectors used for data acquisition to project directly onto the object the inspection information. This approach removes the need to calibrate two separate devices: the one used to acquire the three dimensional shape of the outer surface of the object and the one used to project inspection information on the outer surface thereof, which is simpler for the user and the actual implementation of the device, avoids combining errors from two devices and is more cost efficient. Moreover, it simplifies the computation of the images to be displayed by the light projectors to project the inspection information.

BRIEF DESCRIPTION OF THE DRAWINGS

Other objects, advantages and features will become more apparent upon reading the following non-restrictive description of embodiments thereof, given for the purpose of exemplification only, with reference to the accompanying drawings in which.

DETAILED DESCRIPTION

Figure 1:
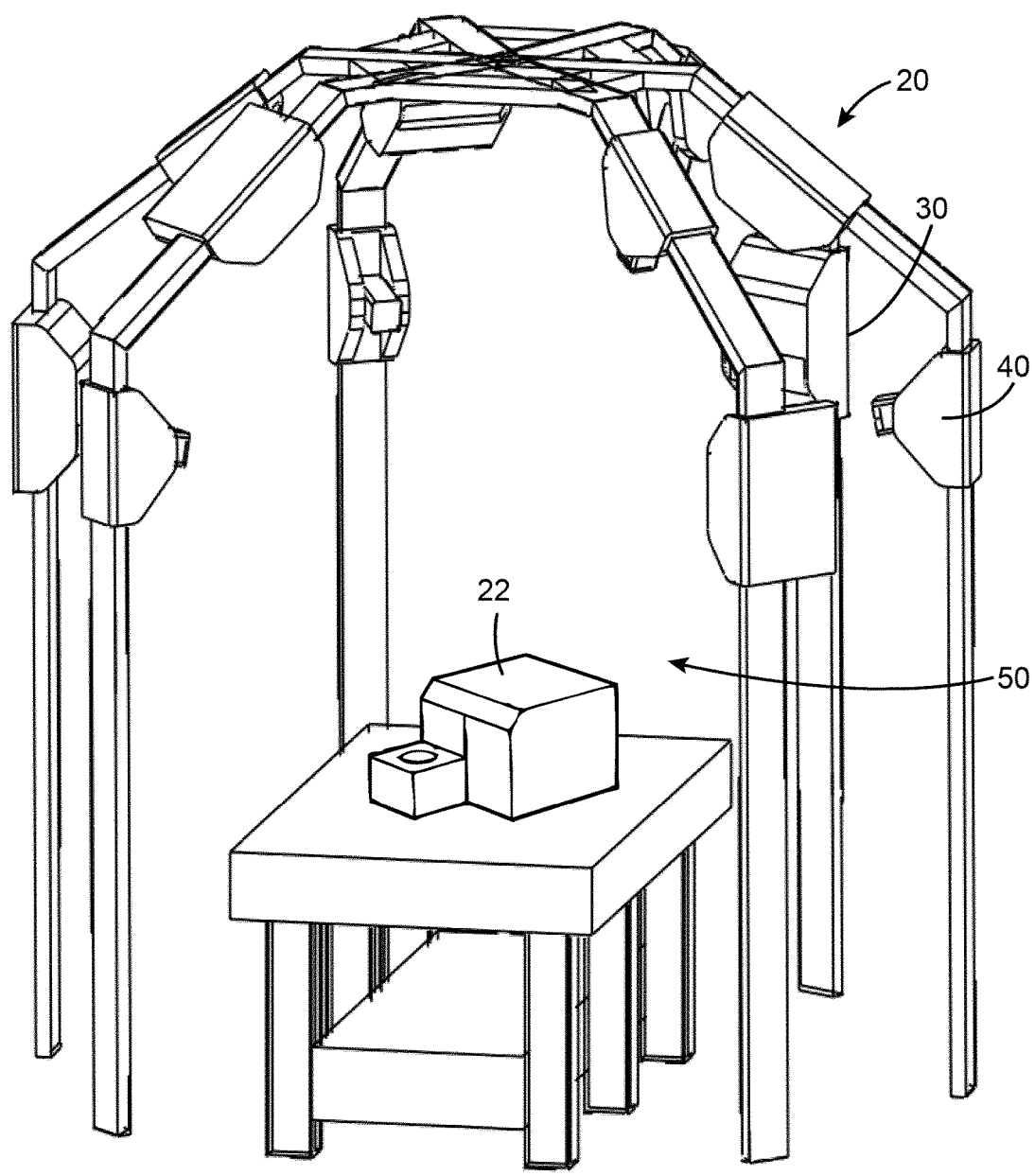
FIG. 1 is a perspective view of a three dimensional inspection system, according to an embodiment.

In the following description, the same numerical references refer to similar elements. The embodiments, geometrical configurations, materials mentioned and/or dimensions shown in the figures or described in the present description are preferred embodiments only, given solely for exemplification purposes.

Moreover, although the embodiments of the three dimensional inspection system and corresponding parts thereof consist of certain geometrical configurations as explained and illustrated herein, not all of these components and geometries are essential and thus should not be taken in their restrictive sense. It is to be understood, as also apparent to a person skilled in the art, that other suitable components and cooperation thereinbetween, as well as other suitable geometrical configurations, can be used for the three dimensional inspection system, as will be briefly explained herein and as can be easily inferred herefrom by a person skilled in the art. Moreover, it will be appreciated that positional descriptions such as "above", "below", "left", "right" and the like should, unless otherwise indicated, be taken in the context of the figures and should not be considered limiting.

Referring generally to FIGS. 1 to 4, there is provided a three dimensional inspection system 20 to perform concurrent inspection of an outer surface of an object 22 and feedback of the inspection results by projection of inspection information data directly on the outer surface of the inspected object 22.

In the course of the present document, the term "object" is used to refer to any part or assembly inspected using the inspection system 20 described herein. A non-limitative list of objects which can be inspected using the inspection system 20 includes mechanical components, assemblies or systems, walls, floors or other structural features, vehicle, diverse pieces of equipment, package, wiring, engine, circuit board, casting, food, tooling, body part, prosthesis, orthosis or the like. It will be readily understood that the object being inspected need not be a complete structure, but can be embodied by a portion, small or large, of any of the above. The outer surface of the object 22 is defined by a plurality of surface points with specific spatial coordinates.

In order to perform the inspection and projection of the inspection information data on the object, the three dimensional inspection system 20 includes at least one light projector 30 and at least one camera 40 positioned such as to jointly define a field of view 50 of the inspection system 20. The field of view of the inspection system can therefore be understood as the area that is covered by the intersection of the camera field of view 51 defined by the at least one camera 40 and the light projector field of view 52 defined by the at least one light projector 30 and where an object can be placed to be inspected by the least one light projector 30 and the at least one camera 40. As will be described in more details below, the same light projector or projectors 30 are used for acquisition of three dimensional object data representative of the outer surface of the object 22 and the projection of inspection information data on the object 22. Hence, it will be understood that the field of view is similar for the acquisition of three dimensional object data representative of the outer surface of the object 22 and the subsequent projection of the inspection information data on the outer surface of the object 22.

In the course of the present document, the expression "three dimensional object data representative of the outer surface of the object" is used to refer to any data that can be acquired from a three dimensional object during inspection of an outer surface thereof. For example and without being limitative, the data acquired can relate to the spatial coordinates of points on the outer surface of the object, to the color of points on the outer surface of the object or the like.

Moreover, in the course of the present document, the term "light projector" is used to refer to devices operative to project light on a surface, such as the outer surface of a three-dimensional object 22. The at least one projector 30 can be controlled such as to regulate the color, intensity, shade or the like of the light projected towards each surface points of the outer surface of the object 22. In an embodiment, the at least one light projector 30 is a video projector, such as off-the-shelf DLP, LCD or CRT video-projector like the BenQ W1000+™, Casio XJ-A251™ or the like, or any custom made light projector. In the case where a plurality of light projectors 30 are present, the light projectors 30 can advantageously be all of a same type, or alternatively different types of projectors can be used in a same inspection system 20.

The at least one light projector 30 defines a plurality of source points. For example, in an embodiment, each light projector 30 may include an array of pixels, and each one of the plurality of source points may correspond to a specific pixel of one of the light projectors 30. One skilled in the art will understand that, in an alternative embodiment, the source points can also correspond to a group of pixels.

In the course of the present document, the term "camera" is used to refer to devices operative to capture, store and transfer images. In an embodiment, the at least one camera 40 can be embodied by a video or a still camera, including industrial cameras from manufacturers such as PointGrey™, Allied Vision Technologies™ or the like, or any commercially available cameras from manufacturers such as Canon™, Sony™, or the like. As with the at least one light projector 30, one skilled in the art will understand that, in an embodiment where a plurality of cameras 40 are provided, different types of camera can be used in the inspection system 20. It will be further understood that in alternative embodiments, different models and/or types of light projectors 30 and cameras 40 can be mixed to together define the inspection system 20.

In an embodiment, the at least one camera 40 is a numeric camera which allows the capture of a numeric image of the outer surface of the object 22. One skilled in the art will understand that, in an alternative embodiment, an analog camera can also be used. However, in such an embodiment, processing of the analog images captured by the analog camera is required to convert the analog images captured into numeric images of the outer surface of the object 22. Therefore, such an embodiment requires an additional conversion step of the analog images which is unnecessary when numeric cameras are used.

Figure 2:
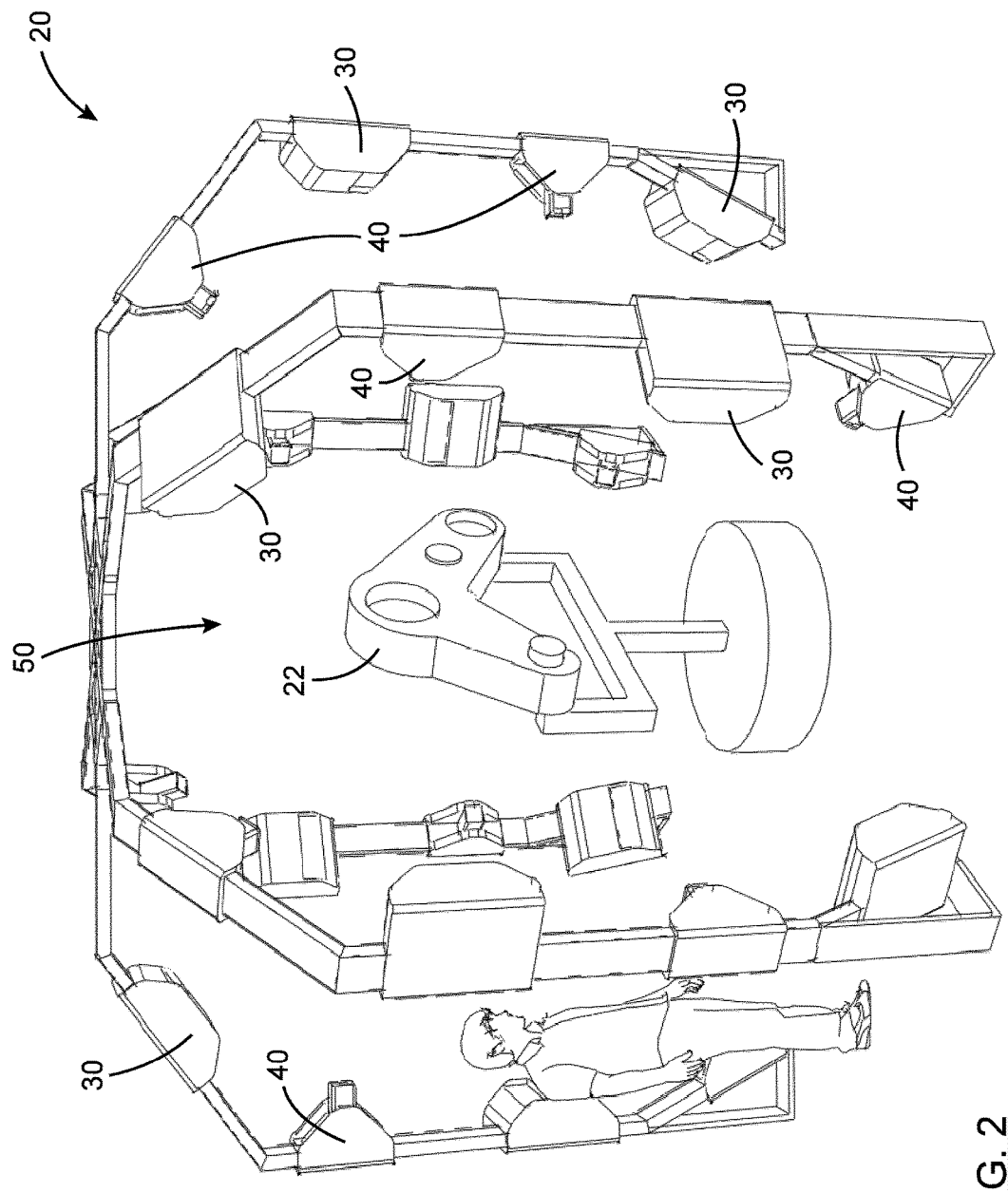
FIG. 2 is a perspective view of a three dimensional inspection system, according to another embodiment.
Figure 3:
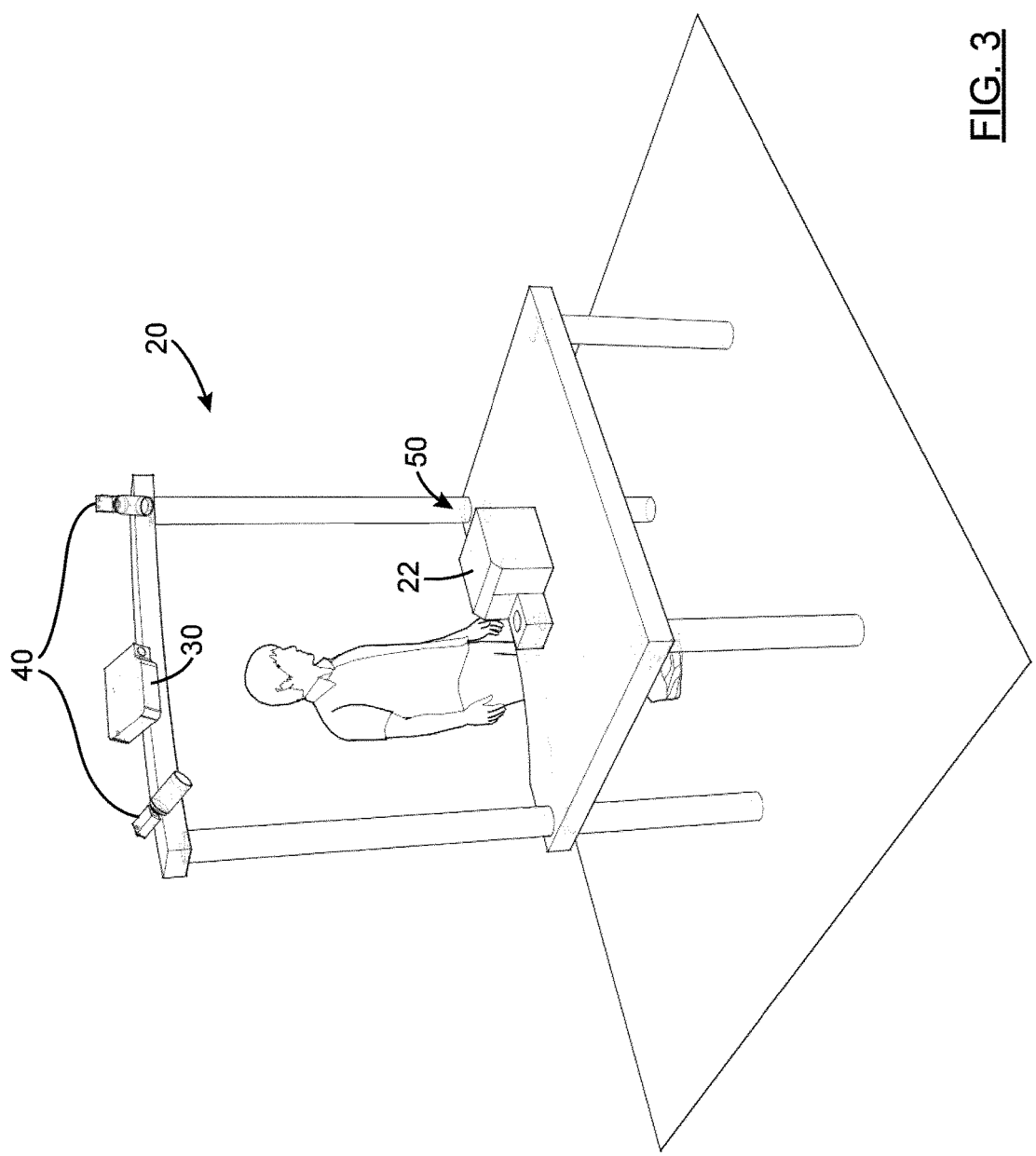
FIG. 3 is a perspective view of a three dimensional inspection system, according to another embodiment.

In the illustrated embodiment of FIGS. 1 and 2, the three dimensional inspection system 20 includes a plurality of light projectors 30 and cameras 40 distributed substantially uniformly around the object. In the embodiment of FIG. 3, the inspection system 20 includes one light projector 30 and two cameras 40. Therefore, it will be understood that, in alternative embodiments, the quantity and position of the at least one light projector 30 and the at least one camera 40 defining the field of view 50 can be varied. For ease of understanding and without being limitative, the at least one light projector 30 will be referred below as the projectors 30 and the at least one camera 40 will be referred below as the cameras 40.

Figure 4:
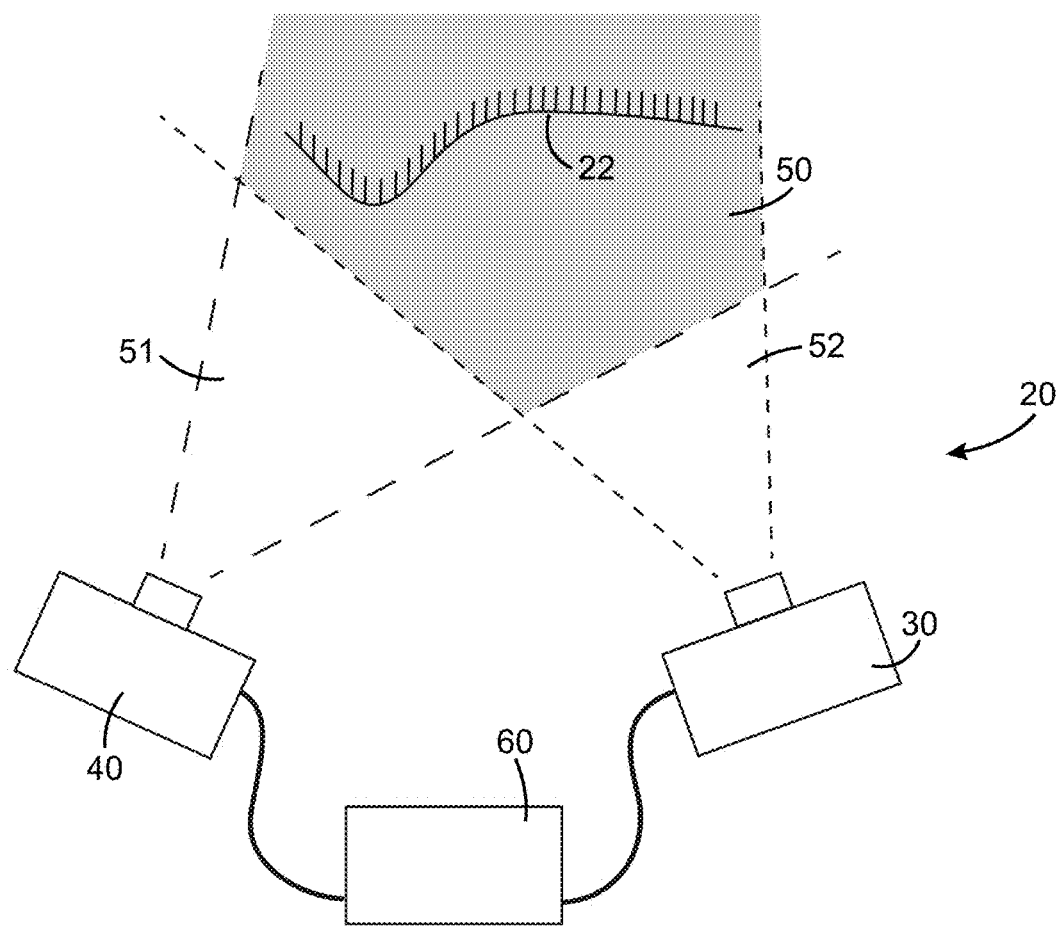
FIG. 4 is a schematic representation of an inspection system, according to an embodiment.

Referring to FIG. 4, the three dimensional inspection system 20 further includes a computer 60 operatively connected to the projectors 30 and the cameras 40, for example and without being limitative, using video cables or other means for transferring data, information and/or graphics between the computer 60, the projectors 30 and the cameras 40. One skilled in the art will understand that the term "computer" is used herein to refer to a general purpose device with a memory and an processor and which can store, retrieve, and process data according to a set of instructions stored in the memory thereof and produce output from the processing of data by the processor. One skilled in the art will understand that the computer 60 can be a stand-alone unit or may consist of a plurality of interconnected units that are operably connected with each other. Interface and network cards (not shown) can be installed in the computer 60 to allow the connection with other computers of a computer network, the cameras 40 and the projectors 30. In an embodiment, a software program installed on the computer 60 manages the processing and input/output required for the acquisition of the three dimensional object data and the projection of the inspection information data. Advantageously, in an embodiment, a user interface of the computer allows the user to start the inspection process, using peripherals such as mouse, keyboards or the like. In an embodiment, subsequent steps of the inspection method, as will be described in more details below, are handled by the software program.

Once again, one skilled in the art will understand that, although one camera 40 and one light projector 30 are connected to the computer 60 in FIG. 4, in alternative embodiments, the number of cameras 40 and light projectors 30 connected to the computer 60 can be varied.

The computer 60 is configured to control the projectors 30 and the cameras 40, in order to acquire three dimensional object data representative of the outer surface of the object 22, generate inspection information data based on the acquired three dimensional object data and project the inspection information data on the outer surface of the object 22. One skilled in the art will understand that the light projectors 30 are controlled such that the light projected therefrom can be varied to perform the acquisition of the three dimensional object data and the projection of the inspection information data. For example and without being limitative, the light projectors 30 can project white light (subsequently acquired by the cameras 40) in order to perform the acquisition of the three dimensional object data, while varying the color, intensity, shade, or the like, of the light projected towards each surface points of the outer surface of the object 22, for each one of the source points, to project the inspection information data on the outer surface of the object 22.

In an embodiment, the three dimensional object data representative of the outer surface of the object 22 positioned within the field of view 50 can be acquired by obtaining the spatial coordinates of the surface points located on the outer surface of the object 22, by triangulation. In such an embodiment, the light projectors 30 and the cameras 40 are calibrated such that the cameras 40 can triangulate, from their known positions, the spatial location of each surface point of the outer surface of the object 22, which is lit by the projectors 30. In other words, the outer surface of the object 22 is lit by the light projectors 30 and cameras 40 are calibrated such as to triangulate the location of the surface points of the object 22 by acquisition of return light from the outer surface thereof.

In an embodiment, the projectors 30 and the cameras 40 are configured to be used as a structured light three dimensional scanner to capture the three dimensional object data representative of the outer surface of the object by triangulation. In such an embodiment, the projection of a particular light pattern designed to facilitate the acquisition of the three dimensional object data is performed by the projectors 30.

One skilled in the art will understand that in alternative embodiments, other physical principles such as interferometry, time of flight, or the like can be used for acquiring the three dimensional object data representative of the outer surface of the object. One skilled in the art will readily understand that the use of such techniques can depend on the target application and the capacity of the light projectors 30 used to provide illumination of the outer surface of the object 22 during the three dimensional object data acquisition process.

In an embodiment, the acquired three dimensional object data relative to the outer surface of the object 22 relates surface points on the outer surface of the object 22 to one or more of the source points of the light projector 30.

In order to perform such relation between the surface points on the outer surface of the object 22 and the one or more of the source points of the light projector 30, in an embodiment, the acquisition of the three dimensional object data representative of the outer surface of the object 22 can be performed by generating a point cloud of surface points where three dimensional spatial coordinates match corresponding points on the surface of the inspected object 22. Each point of the point cloud originates from a specific and known source point, such as a pixel in a specific projector 30, such that there is a direct relationship between a surface point and a specific source point of a specific projector. One skilled in the art will understand that, in order to generate the point cloud, a pre-calibration of the cameras 40 is required. In an embodiment, a pre-calibration of the light projectors 30 is also required. The calibration is performed as an anterior step using existing calibration techniques. For example, the calibration can be performed by placing an object of known physical characteristics in the field of view 50. Calibration techniques are generally well-known to those skilled in the art and need not be described further herein. The point cloud may also include additional data gathered from the object, such as the color of each surface point, for example.

As previously mentioned, once the three dimensional object data representative of the outer surface of the object 22 has been acquired, the computer 60 processes the three dimensional object data and generates the inspection information data. As previously mentioned, the generated inspection information data can be any information that can be obtained by processing the three dimensional object data, including the actual position of the inspected object 22, its actual shape, its actual shape compared to a reference, its color, its color compared to a reference, a deviation resulting from defect or quality of the object 22 or any information related to its assembly. For example and without being limitative, the inspection information data can relate to the coordinates to where a next sub-assembly must be placed on the inspected object 22, the identification of a region that requires rework, a deviation from targeted reference dimensions of the object 22 or a deviation from a targeted color in a section of the object.

In an embodiment, in order to generate the inspection information data, the generated point cloud is used to determine dimensional or visual deviations of the object 22, if any, as compared to a known reference object. In an embodiment, the reference object is a three-dimensional object imported into the computer 60, such as a Computer-Aided Design (CAD) of the inspected object 22. In order to perform the determination of the dimensional or visual deviations, the computer 60 performs a computation of the alignment of the point cloud with the reference object, using known algorithms such as "Iterative Closest Points". Once the reference object and the point cloud are aligned, comparison of the points of the point cloud and the corresponding points of the reference object are performed to determine deviations and identify dimensional or visual defect of the inspected object 22 from which the point cloud has been generated.

As will be described in more details below, the computer 60 of the three dimensional inspection system 20 also controls the light projectors 30 to subsequently project the inspection information data on the object 22. The light projectors 30 are therefore jointly controlled to project a specific light point from a source point on each one of the desired surface points on the outer surface of the object 22.

In an embodiment, the projected inspection information data can advantageously be embodied by variations in color of the light projected by the projectors to project inspection information data on the outer surface of the object 22. One skilled in the art will however understand that, in alternative embodiments, other types of variations in the projected light can be used to represent the inspection information data, such as and without being limitative, intensity, shades, or the like.

Given that in the above described three dimensional inspection system 20, the same light projectors 30 are used for acquiring the three dimensional object data and for the projection of the inspection information data on the outer surface of the inspected object 22, the determination of the image to be displayed by the projectors 30 to project the generated inspection information data on the outer surface of the object 22 can be performed without requiring further calibration of the projectors 30. Indeed, as previously mentioned, each one of the surface points on the outer surface of the object 22 acquired through the three dimensional object data relates to a specific source point for each one of the projectors 30, such that there is a direct relationship therebetween. Therefore, the color to output from a specific source point, such as a pixel, of a specific projector can be determined by the computer 60 by using the color that the corresponding surface point should have according to the inspection information data. For example and without being limitative, if a text message is to be displayed on the outer surface of the object 22, the color of each surface point is that of the closest point on the outer surface of the reference object on which the corresponding text message is juxtaposed.

In an embodiment where the inspection information data relates to deviation information, the color of each surface point can be obtained from a predetermined colormap matching colors with corresponding distances between the surface point and the closest point of the reference object. Once the color of a surface point has been determined, once again the color to output from a specific source point, such as a pixel, of a specific light projector 30 can be determined by the computer 60 by using correspondence between the surface points and the source points.

As can be understood, the use of the same light projectors 30 for both the capture of the three dimensional object data relative to the outer surface of the object 22 and the projection of the inspection information data on the object 22 allows the inspection information data to be projected onto the outer surface of the object 22 more rapidly. For example and without being limitative, in the above example of applications where the object needs to be reworked, this allows instant feedback to be provided to the workers, thereby allowing an advantageous in-process quality control.

In an embodiment, the light projectors 30 and/or the cameras 40 can be movable relative to the object 22 placed in the field of view 50, for example and without being limitative, to modify the field of view 50 or provide more flexibility to the three dimensional inspection system 20. One skilled in the art will understand that, in an embodiment (not shown), the light projectors 30 and/or the cameras 40 can be mounted on a support which allow the light projectors 30 and/or the cameras 40 to move simultaneously relative to the object 22 placed in the field of view 50 such as to maintain a similar relative positioning between the light projectors 30 and/or cameras 40 mounted on the support. In an alternative embodiment the light projectors 30 and/or cameras 40 can be moved independently from one another.

One skilled in the art will understand that when the light projectors 30 and/or cameras 40 are moved during inspection of the object 22, the three dimensional inspection system 20 can independently sense and determine the displacement which occurred and consequently adapt the display of the light projectors 30 to project the inspection information data correctly on the object 22. In an embodiment where the light projectors 30 and/or cameras 40 are moved between the inspection of the object 22 and the projection of inspection information data thereon, the displacement must be calculated and processed in order to allow the accurate modification to be performed to the relation between the surface points of the object 22 and the source points of the projectors 30 for the accurate projection of the inspection information data on the outer surface of the object 22.

In order to perform the sensing and determination of the displacement of the light projectors 30 and/or cameras 40, for example and without being limitative, in an embodiment (not shown), the three dimensional inspection system 20 further includes an external positioning system (not shown) operatively connected to the computer 60. External positioning systems are commonly used to track specific elements and determine the spatial position of these elements and the operation of such external positioning systems is well known to those skilled in the art. As will therefore be easily understood by one skilled in the art, the external positioning system can therefore evaluate the spatial position of the projectors 30 and/or cameras 40 before and after the movement thereof. Displacement data for the projectors 30 and/or cameras 40 can be computed, based on these positions, and subsequently be used to adjust the inspection information data, in view of the movement of the light projectors 30 and/or cameras 40, for the accurate projection of the inspection information data on the outer surface of the object 22.

In an embodiment where images projected by concurrent projectors 30 overlap on the outer surface of the object 22, overlap identification can be performed by the computer 60. In an embodiment, overlap identification can be performed by the display of a white image by each one of the projectors 30 in turn and determination of the overlap locations using images of the cameras 40. Once the overlap identification has been performed, fading of specific projectors 30 can be performed on the identified overlap locations to avoid difference in brightness across the outer surface of the object 22 during the projection. In an alternative embodiment, overlap can also be determined when determining the image that each projector 30 needs to display in order to project the desired inspection information data on the outer surface of the object 22. The intensity of each pixel where overlap is determined can therefore be balanced to avoid difference in brightness across the outer surface of the object 22 during the projection. Such an embodiment can however be problematic when doing rework on an object 22 concurrently with projection of the inspection information data, as this can cause blind spots for a specific projector 30. Hence, one skilled in the art will understand that, in alternative embodiments, no overlap identification and corresponding adjustment of the light projectors can be performed to alleviate the above-described blind spot issue.

Figure 5:
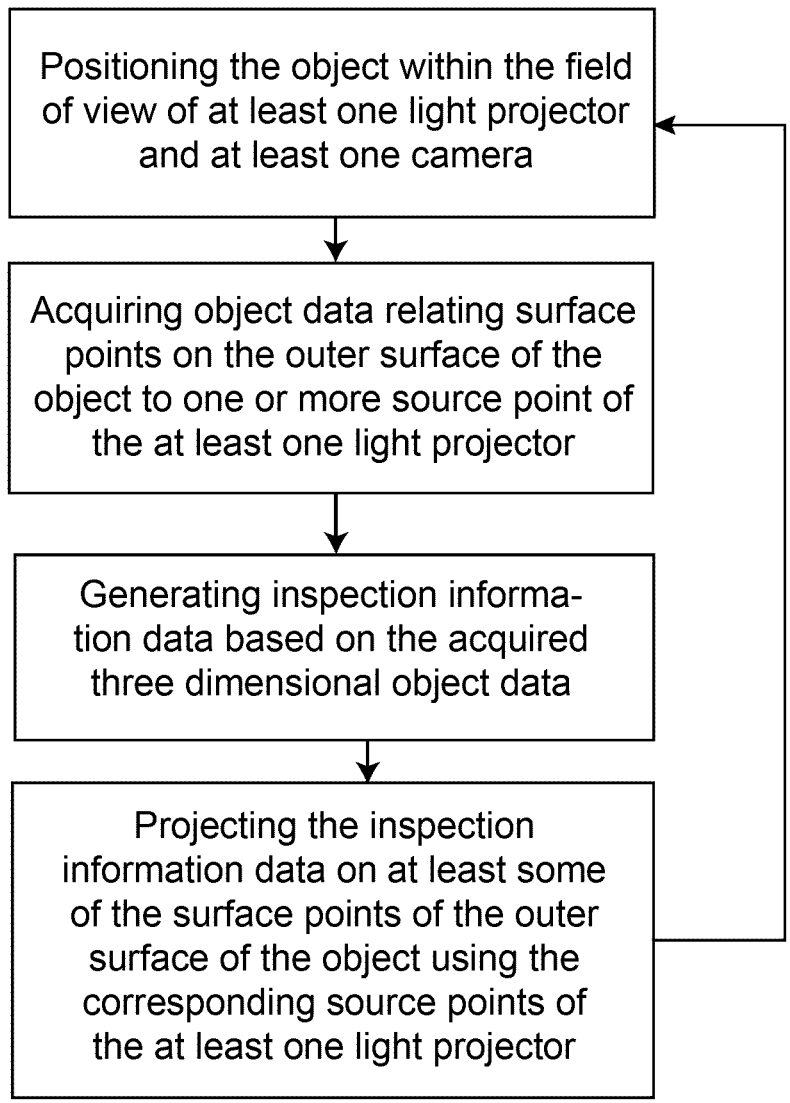
FIG. 5 is a Flowchart representation of the steps of an inspection method, according to an embodiment.

Now referring to FIG. 5, a method for inspecting an object, according to an embodiment, will be described in more details below. In an embodiment, the method is performed using the above described three dimensional inspection system or other configurations thereof providing the required functionalities.

The method includes the steps of positioning the object within the field of view of the three dimensional inspection system comprising the light projectors 30 and the cameras 40. Once the object has been positioned properly, the light projectors 30 emit light towards the object 22 and the cameras 40 capture return light such that three dimensional object data representative of the outer surface of the object 22 is acquired. As mentioned above, the three dimensional object data relates surface points on the outer surface of the object 22 to one or more source points of the light projectors 30. The method also includes the further step of generating inspection information data based on the acquired three dimensional object data and projecting the inspection information data on the outer surface of the object 22. Once again, the projection of the inspection information data on the outer surface of the object 22 is performed by projecting the inspection information data on at least some of the surface points of the outer surface of the object 22 using the corresponding source points of the light projectors.

One skilled in the art will understand that, in an embodiment, the object may subsequently be moved and the above-described steps may be repeated, for example and without being limitative, when the three dimensional inspection system 20 can only inspect and/or project the inspection information data on a portion of the outer surface of the object 22.

All of the above-mentioned characteristics related to the acquisition of three dimensional object data representative of the outer surface of the object 22, generation of the inspection information data and the projection of the inspection information data on the outer surface of the object 22 apply to the corresponding steps of the method and will not be repeated herein for ease of understanding.

Several alternative embodiments and examples have been described and illustrated herein. The embodiments of the invention described above are intended to be exemplary only. A person skilled in the art would appreciate the features of the individual embodiments, and the possible combinations and variations of the components. A person skilled in the art would further appreciate that any of the embodiments can be provided in any combination with the other embodiments disclosed herein. It is understood that the invention can be embodied in other specific forms without departing from the central characteristics thereof. The present examples and embodiments, therefore, are to be considered in all respects as illustrative and not restrictive, and the invention is not to be limited to the details given herein. Accordingly, while specific embodiments have been illustrated and described, numerous modifications come to mind without significantly departing from the scope of the invention.

The invention claimed is:

1. A three dimensional inspection system for inspecting an outer surface of an object, the inspection system comprising:
    at least one light projector and at least two cameras jointly defining a field of view of the inspection system; and
    a computer operatively connected to the at least one light projector and the at least two cameras, the computer being configured to:
        acquire three dimensional object data representative of the outer surface of the object positioned in the field of view through projection of light thereon by the at least one light projector and acquisition of return light by the at least two cameras, the three dimensional object data relating surface points on the outer surface of the object to one or more source points of the at least one light projector;
        generate inspection information data based on the acquired three dimensional object data; and
        project the inspection information data on at least some of the surface points of the outer surface of the object using the corresponding source points of the at least one light projector; determination of an image to be displayed by the at least one light projector, to project the generated inspection information data on the outer surface of the object, being performed without requiring calibration of the at least one light projector.

2. The three dimensional inspection system of claim 1, wherein the source points of the at least one light projector each comprise a pixel of one of the at least one light projector.

3. The three dimensional inspection system of claim 1, wherein the three dimensional object data comprises a point cloud of three dimensional spatial coordinates matching corresponding ones of the surface points on the outer surface of the object.

4. The three dimensional inspection system of claim 3, wherein the inspection information data is based on deviations between the spatial coordinates of the point cloud and a reference object.

5. The three dimensional inspection system of claim 1, wherein at least one of the least one light projector and the at least two cameras is moveable relative to the object and wherein the computer is further configured to:
    sense the movement of the at least one of the at least one light projector and the at least two cameras; and
    adapt the projection of the inspection information data according to the sensed movement.

6. The three dimensional inspection system claim 1, wherein the at least two cameras comprise numeric cameras capturing numeric images of the object.

7. The three dimensional inspection system of claim 1, wherein the inspection system includes at least two light projectors and wherein the computer is further configured to determine overlap locations of a light projected by the at least two light projectors on the outer surface of the object and fade the light projected by at least one of the at least two light projectors at the overlap locations.

8. The three dimensional inspection system of claim 1, comprising a plurality of light projectors and cameras.

9. The three dimensional inspection system of claim 8, wherein the plurality of light projectors and cameras are substantially uniformly distributed around the object.

10. A method for inspecting an outer surface of an object, the method comprising the steps of:
    positioning the object within a field of view of at least one light projector and at least two cameras;
    acquiring three dimensional object data representative of the outer surface of the object positioned in the field of view through projection of light thereon by the at least one light projector and acquisition of return light by the at least two cameras, the three dimensional object data relating surface points on the outer surface of the object to one or more source points of the at least one light projector;
    generating inspection information data based on the acquired three dimensional object data; and
    projecting the inspection information data on at least some of the surface points of the outer surface of the object using the corresponding source points of the at least one light projector; determination of an image to be displayed by the at least one light projector, to project the generated inspection information data on the outer surface of the object, being performed without requiring calibration of the at least one light projector.

11. The method for inspecting an object of claim 10, further comprising the step of generating a point cloud of three dimensional spatial coordinates matching corresponding ones of the surface points on the outer surface of the object.

12. The method for inspecting an object of claim 11, wherein the step of generating the inspection information data comprises the sub-step of determining a deviation between corresponding spatial coordinates of the point cloud and a reference object.

13. The method for inspecting an object of claim 10, further comprising the steps of:
    sensing the movement of at least one of the least one light projector and the at least two cameras; and
    adapting the projection of the inspection information data according to the sensed movement.

14. The method for inspecting an object of claim 10, wherein at least two light projectors are provided and further comprising the steps of:
    determining overlap locations of a light projected by the at least two light projectors on the outer surface of the object; and
    fading the light projected by at least one of the at least two light projectors at the overlap locations.

* * * * *